United States Patent

Eisman et al.

Patent Number: 5,259,388
Date of Patent: Nov. 9, 1993

[54] MULTIPLE ELECTRODE MYOGRAPHIC PROBE

[76] Inventors: Eugene Eisman, 3209 N. Summit Ave., Milwaukee, Wis. 53211; Jeannette Tries, 3125 S. 57th St., Milwaukee, Wis. 53219

[21] Appl. No.: 734,406

[22] Filed: Jul. 23, 1991

[51] Int. Cl.⁵ .................................. A61B 5/04
[52] U.S. Cl. ............................ 128/733; 128/742
[58] Field of Search ........... 128/733, 788, 774, 747, 128/778, 780, 642, 639

[56] References Cited

U.S. PATENT DOCUMENTS

| | | | |
|---|---|---|---|
| 3,403,684 | 10/1968 | Stiebel et al. | 128/788 |
| 3,800,800 | 4/1974 | Garbe et al. | 128/788 |
| 3,933,147 | 1/1976 | Du Vall et al. | 128/788 |
| 4,058,116 | 11/1977 | Bucalo | 128/642 |
| 4,396,019 | 8/1983 | Perry, Jr. | 128/733 |
| 4,564,024 | 1/1986 | Wohler, Jr. | 128/788 |
| 4,688,575 | 8/1987 | Du Vall | 128/422 |
| 4,887,610 | 12/1989 | Mittal | 128/788 |
| 4,909,263 | 3/1990 | Norris | 128/788 |
| 5,046,511 | 9/1991 | Maurer et al. | 128/788 |
| 5,125,406 | 6/1992 | Goldstone et al. | 128/642 |

FOREIGN PATENT DOCUMENTS 2601254  1/1988 France .................. 128/788

Primary Examiner—Max Hindenburg
Assistant Examiner—Guy V. Tucker
Attorney, Agent, or Firm—Quarles & Brady

[57] ABSTRACT

An electrode assembly simultaneously measures myographic signals for proximal and distal muscles of the anal canal or the like by means of a first and second electrode pair displaced along an insulating support for fitting within the anal canal. In a first embodiment, the insulating support is tubular for channeling conductors from the electrodes to outside of the canal. In a second embodiment, the first and second electrode pairs are formed from conductive paint and connected to the distal end of the insulating support by means of pathways of conductive paint coated with insulating paint. The use of the probe provides a highly resolved schedule of the interaction of the various muscles of the anal canal needed for accurate diagnosis of injury or weakening of these muscles and rehabilitation of these muscles.

7 Claims, 2 Drawing Sheets

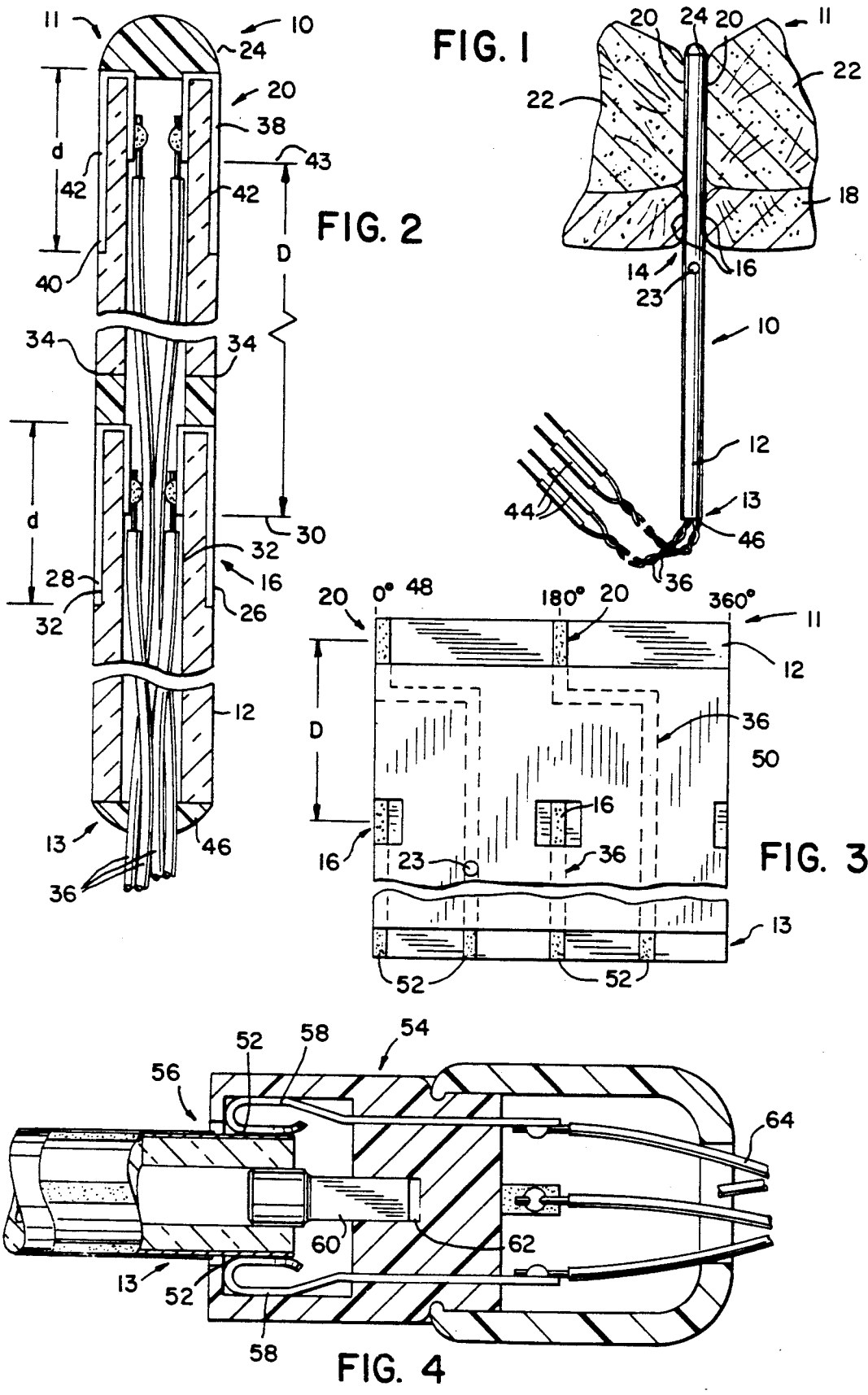

MULTIPLE ELECTRODE MYOGRAPHIC PROBE

FIELD OF THE INVENTION

The present invention relates to an electrode assembly for measuring electrical signals produced by the muscles of the pelvic floor and, in particular, by the muscles of the distal and proximal parts of the external anal sphincter (EAS).

BACKGROUND OF THE INVENTION

The muscles of and surrounding the anal canal are critical to normal bowel and bladder function. The anal canal will be considered to include the tissue from the anal verge, where the anal canal opens to outside of the body, to the recto-anal juncture.

When the muscles of the anal canal are weakened or damaged, as a result of disease, trauma, neuropathy, post-surgical injury, and the like, a variety of disorders such as constipation, diarrhea, incontinence, hemorrhoids, or rectal prolapse may occur. Some of these muscles are innervated by the somatic nervous system and thus the possibility exists that they may be rehabilitated by means of biofeedback techniques which help exercise or retrain these muscles. Nevertheless, the proper functioning of these muscles is not well understood nor easily studied. As a consequence, it is difficult to diagnose the cause of a particular disorder or to identify the muscles involved and thus to determine the proper treatment and the likelihood of successful rehabilitation.

Myographic probes for insertion in the anal canal which provide general information as to the muscle activity in this region, have produced disappointing results as far as diagnosing various disorders of the anal canal.

One promising technique for studying the muscles of the anal canal is digital subtraction defecography, a radiographic technique which can produce multiple x-ray images of these muscles separated by an interval of about 1 to 1 ½ seconds. By studying the sequence of these images it is thought that the coordination of the various muscles of the anal canal and the muscles in its proximity (together, "the anal canal group") may be better understood to establish a guide for treatment and a basis for accurate prognosis. It is possible that early diagnosis of the functional disorder of the muscles of the anal canal can suggest preventative measures to arrest or reverse this disorder and thereby to avoid further and more serious organic damage.

SUMMARY OF THE INVENTION

The present invention employs a specially constructed electrode to provide independent myographic data revealing the interaction and coordination of the different muscles of the anal canal group. It has been determined, by studies conducted with the present invention, that the muscles of this group operate in a complex and coordinated fashion not apparent in instruments measuring the combined reaction of these muscles, or measuring the muscles on intervals of one second or more. The present invention, employing myographic techniques, can provide an accurate indication of the activities of the separate muscle groups with a time resolution of much less than one-tenth of a second. With such resolution and separation, the activities of the muscles in this group may be more accurately characterized, leading to potential improvement in the diagnosis and treatment of a range of disorders such as incontinence, diarrhea and constipation.

Specifically, an elongate insulating support is received in a position into the anal canal. A first electrode pair is positioned on the outer surface of the insulating support for receiving myographic signals from the distal muscles of the canal. A second electrode pair is positioned on the outer surface of the insulating support and spaced from the first electrode pair to receive myographic signals from the proximal muscles of the canal.

It is thus one object of the invention to provide independent and high resolution data for the distal and proximal portions of the anal canal. The myographic electrodes have a response time limited in practice only by the sampling rate of the connected equipment. Separate pairs of electrodes permit activity in the proximal and distal portions of the anal canal to be isolated and examined separately. The ability to make such measurements has revealed unexpected and diagnostically important short-term interaction among the muscles of the anal canal group, as will be described in detail below.

In one embodiment, the conductors of the first and second electrode pairs are conductive paint on the outer surface of the insulating support, and the electrode pairs which communicate with an end of the insulating support, outside of the canal, by means of pathways of conductive paint.

It is thus another object of the invention to produce a simple and inexpensive means for diagnosing disorders of the anal canal and associated structures. The use of a myographic probe simply evaluates the relationship of muscular activity along the length of the anal canal without the expense of radiographic studies or the patient's exposure to potentially harmful ionizing radiation. The conductive paint may be printed onto inexpensive insulating materials to construct a hygienic and disposable electrode. This low-cost method and apparatus potentially increases the availability of accurate diagnoses to patients and, therefore, increases the possibility of successful treatment.

In the preferred embodiment, a set of electrode assemblies is used where the spacing between the distal and proximal electrode pairs is different for each electrode assembly, and the spacing increases from a first given electrode assembly to a last given electrode assembly.

It is another object of the invention to provide a simple means for accommodating variations in the dimensions of the anal canal among patients and to accurately quantify the myographic measurements. The use of separate probes eliminates seams and the resulting sterilization problems that would result from an extensible electrode system. Further, the fixed probe lengths provide an accurate gaging of the separation between the probe electrodes, improving the quantification and accuracy of the diagnosis.

The foregoing, and other objects and advantages of the invention, will appear from the following description. In the description, reference is made to the accompanying drawings which form a part hereof, and in which there is shown by way of illustration, preferred embodiments of the invention. Such embodiments do not necessarily represent the full scope of the invention, however, and reference is made, therefore, to the claims herein for interpreting the scope of the invention.

BRIEF DESCRIPTION OF THE DRAWINGS

FIG. 1 is an elevational view of the electrode assembly of the present invention in place within the anal canal;

FIG. 2 is a cross-sectional view of the electrode assembly of FIG. 1 showing placement of the electrode pairs and their connection to flexible leads;

FIG. 3 is a panoramic or "unrolled" depiction of a second embodiment of the electrode of FIG. 1 employing conductive and insulating paints for the electrode pairs, and the connecting conductive leads;

FIG. 4 is a cross-sectional view of a connector for connecting to the probe of FIG. 3.

DETAILED DESCRIPTION OF THE PREFERRED EMBODIMENT

Figure 5:
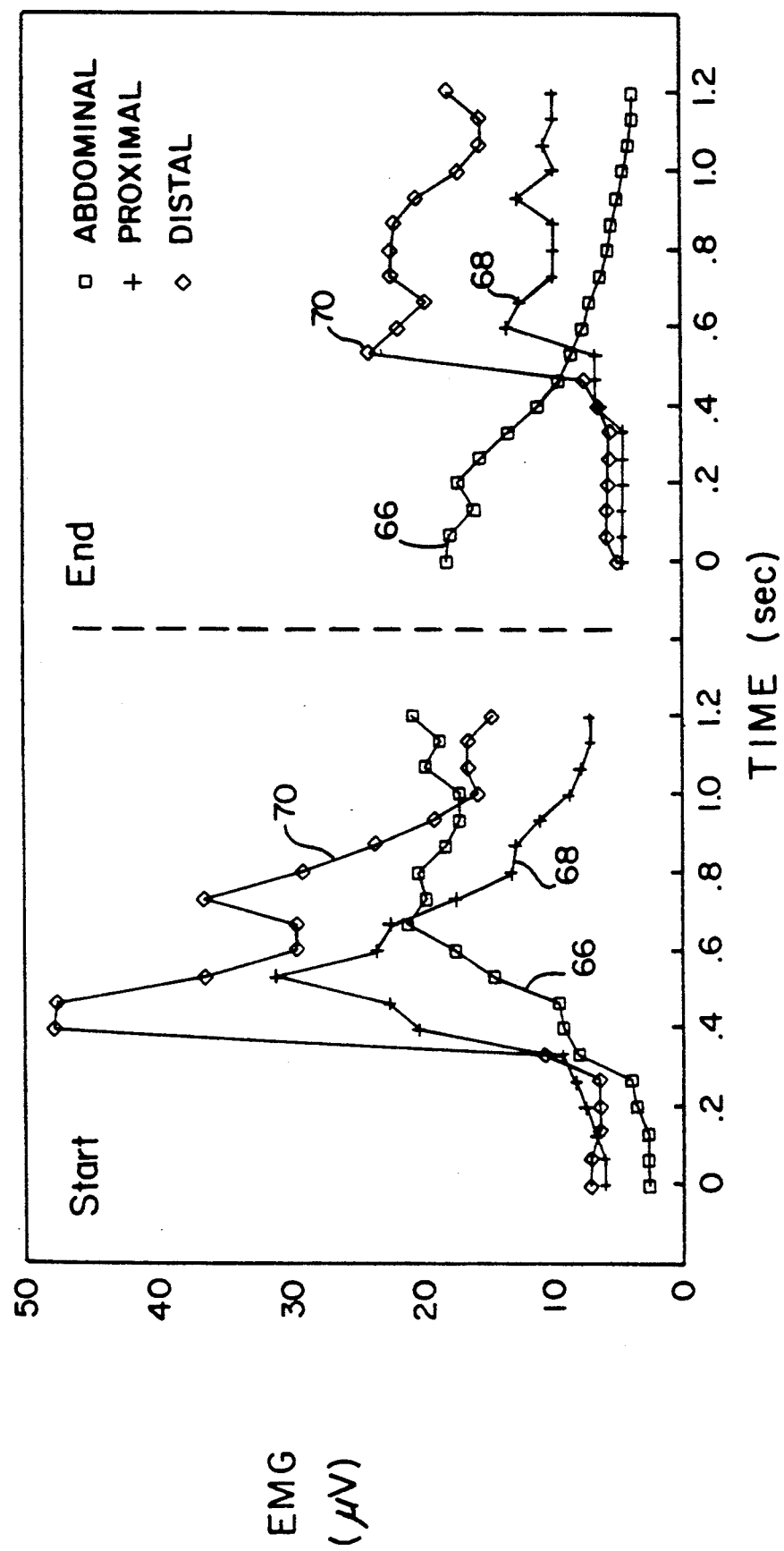
FIG. 5 is a chart showing myographic signals as recorded by the electrode of the present invention and showing the interrelationship of the muscle groups of the anal canal in an asymptomatic individual as provided by the present invention.

Referring to FIG. 1, an electrode assembly 10 includes a generally cylindrical and tubular insulating support 12 having a first end 11 for being received within the anal canal 14 and a second end 13 extending outside of the anal canal 14. When the first end 11 of the insulating support 12 is positioned within the anal canal 14, a first electrode pair 16 exposed on opposite sides of the insulating support 12, contacts the distal muscles 18 just within the anal verge or outer surface of the anal canal 14.

When the first electrode pair 16 is in contact with the distal muscles 18 of the anal canal 14, a second electrode pair 20, also exposed on opposite sides of the insulating support 12, contacts the proximal muscles 22 of the anal canal 14, such proximal muscles 22 being removed from the anal verge along the anal canal 14, further within the body than the distal muscles 18.

The insulating support 12 is positioned within the anal canal 14 by grasping the insulating support 12 at embossment 23 positioned on a length of the insulating support 12 remaining outside of the anal canal 14 when the multiple electrode probe 10 is in place within the anal canal 14. The embossment 23 may be located tactilely and serves to control the depth of insertion of the insulating support 12, which is otherwise open, and the rotational orientation of the insulating support 12.

The first end 11 of the insulating support 12 received by the anal canal 14 is capped by a hemispherical tip 24 which serves to seal the end 11 of the tubular insulating support 12 and to reduce abrasion of the anal canal 14 by the edges of the end 11 of the tubular insulating support 12. The first and second conduction strips 26 and 28 are thus separated on opposite sides of the insulating support 12 to sensing and myographic potentials.

Referring to FIG. 2, the first electrode pair 16 is formed of a first and second conductive strip, 26 and 28, respectively, extending longitudinally along the insulating support 12 a distance d and received within milled flats 32 cut in the outer wall of the insulating support 12 so as to permit the first and second conductive strips 26 and 28 to lie flat against the outside of the insulating support 12.

The upper ends of each conductive strip 26 and 28, near first end 11, pass through the walls of the insulating support, by means of holes 34, and extend inside the tubular insulating support 12 where they are attached to conductive leads 36. A separate conductive lead 36 is attached to the first conductive strip 26 and the second conductive strip 28.

Correspondingly, the second electrode pair 20 is formed of a third and fourth conductive strip, 38 and 40, also extending a length d along the axis of the tubular insulating support 12. The third and fourth conductive strips 38 and 40 are also received by milled flats 42 similar to the milled flats 32 for the first and second conductive strips 26 and 28. The upper ends of the conductive strips 38 and 40 are folded over the first end 11 of the insulating support 12 prior to the placement of the hemispherical tip 24 thereon and thereby connected to the inside of the tubular insulating support 12. Separate conductive leads 36 are attached to each of the third and fourth conductive strips 38 and 40 inside of the insulating support 12.

Referring again to FIG. 1, the conductive leads 36 from the first through fourth conductive strips 26, 28, 38 and 40 proceed through the interior of the tubular insulating support 12 away from the first end 11 and out the second end 13 of the insulating support 12 to be terminated by a set of four connectors 44. The connectors 44 may be received by corresponding connectors of an electro-myographic recording device (not shown) for sampling and recording the myographic data received from the probe 10 as is generally understood in the art. The point of exit of the conductive leads 36 at the second end 13 is sealed with a sealant 46 so as to prevent the entrance of moisture into the center of the insulating support 12.

The insulating support 12 is preferably constructed of a rigid thermoplastic material suitable for use in medical applications such as FDA compliant acrylic and has an outside diameter of ¼". The conductive strips 26, 28, 38 and 40 are adhesive coated, copper foil 1 cm by 0.25 cm, pressed into the milled flats 32 and 42 respectively. The hemispherical cap 24 and the sealant 46 are formed from a medical grade silicon rubber. Conductors 36 are preferably 32-gauge, 5-strand copper wire with an insulating cover as is understood in the art and are soldered to the conductive strips 26, 28, 38 and 40 at those ends of those conductive strips protected within the tubular insulating support 12.

Each conductive strip 26, 28, 38 and 40 has associated with it a separate conductive lead 36 to permit the myographic potential across conductive strips 26 and 28 to be measured separately from the electro-myographic potential across conductive strips 38 and 40. Further the conductive strip 26 and 28 of the first electrode pair 16 are separated from the conductive strips 38 and 40 of the second electrode pair 20 by a distance D along the anal canal 14 as measured between inner edges 32 and 43 of the electrode pairs 16 and 20. Thus, the electromyographic signals of the distal muscles 18 may be measured by the first electrode pair 16 independently from the electro-myographic signals of the proximal muscles 22 which may be measured by the second electrode pair 20. The electro-myographic activity of both the proximal and distal muscles 18 and 22, however, may be measured simultaneously on a "real time" basis. The separation distance D ensures that these measurements are independent from one another.

The diameter of the tubular insulating support 12 is chosen to be larger than the contracted state of the anal canal 14 thus insuring a degree of compression of the tissues of the distal and proximal muscles 18 and 22 against the first electrode pair 16 and second electrode pair 20 for good electrical contact.

A set of multiple electrode probes 10 are constructed as described above with varying distances D. In a set of ten probes 10, the first probe 10 has the first and second electrode pairs 16 and 20 separated by a distance D of 1 cm. The distance D increases by one-half centimeter for each of the ten probes 10. The length of the tubular insulating supports 12 increases correspondingly for each probe 10 so as to preserve constant the length of the insulating support 12 external to the body when the probe 10 is inserted in the anal canal 14.

Referring to FIG. 3, in an alternative embodiment, the first and second electrode pairs 16 and 20 are formed from a conductive paint 48 printed on the outside of the tubular insulating support 12. Here, the insulating support 12 may be flexible provided its diameter is small. Likewise, the conductive leads 36 are simple continuations of the path of the conductive paint 48 down along the outside of the insulating support 12. The conductive paint 48 is covered with an insulating paint 50 for all portions except for the areas corresponding to the conductive strips 26, 28, 38, and 40, of the first and second electrode pairs 16 and 20 and for a band around the circumference of the tubular support 12 at the second end 13 outside of the anal canal 14. The conductive paint 48 exposed by the absence of insulating paint 50 at the second end 13 provides a set of four contact surfaces 52 for connecting the electrode probe 10 to external monitoring equipment (not shown).

Referring now to FIGS. 3 and 4, a connector 54 receives the second end 13 of the tubular insulating support 12 within a cylindrical orifice 56. Contacting springs 58, within the connector 54, are compressed, by the insertion of the insulating support 12 within the orifice 56, against contact surfaces 52. The contact surfaces 52 are spaced at 90° intervals around the insulating support 12 to correspond with the spacing of the contacting springs 58 within the connector 54.

The rotational orientation of the insulating support 12 with respect to the connector 54 is ensured by means of a key 60 having a first end fitting within the bore of the tubular insulating support 12, and a second end received by a slot 62 in the base of the connector 54, such that the key 60 engages the slot 62 with insertion of the insulating support 12 into the orifice 56 of the connector 54 only when the contact surfaces 52 are aligned with the appropriate contacting springs 58. The other ends of the contacting springs 58 not contacting the contact surfaces 52 are connected to leads 64 to the monitoring equipment (not shown).

It will be understood from this description that the electrode probe 10, absent the connector 54, is readily manufactured from inexpensive parts and with efficient manufacturing techniques so as to be practically disposable. The more complex connector 54, remaining outside of the body removed from the anal canal 14, may be reused. Further, the contacting springs 58 are designed to have a wiping action with the contact surfaces 52 to insure good electrical contact. The contact surfaces 52 will abrade in preference to the contacting springs 58 increasing the life of the contacting springs 58 without measurably effecting the reliability of the disposable electrode probe 10.

Conductive paint 48 may be a silver powder combined with an organic binder, as is well known, such as polymeric conductor composition 5008 manufactured by Du Pont Electronics of Wilmington, Del., and the insulating paint 50 may be 5014 UV curable dielectric, also manufactured by Du Pont Electronics. Both of these materials may be printed onto the cylindrical surface of the insulating support 12 as will be understood by those of ordinary skill in the art.

In this embodiment, the lumen of the insulating support 12 is open, and if desired, a small balloon catheter may be inserted through an auxiliary hole (not shown) in the wall of the insulating support 12 to provide rectal distension during the myographic measurements.

Referring now to FIG. 5, data taken from the probe 10 of the present invention for an asymptomatic subject is shown. Plotted is electro-myographic data ("EMG") 66, 68, and 70 from the subject's abdominal muscles and proximal and distal muscles 22 and 18, respectively, for the start and end of a "pushing" which simulates defecation. The abdominal signal is taken by means of conventional surface electrodes.

At the start of the pushing, the abdominal muscles are tightened as indicated by the increasing EMG signals 66. There is a reflexive increase in the EMG signals 68 and 70 from the proximal and distal parts of the anal sphincter 14. The distal EMG signal 70 reaches a peak first, then the proximal EMG signal 68, and finally the abdominal EMG signal 66. Within one second, the distal and proximal signals 70 and 68 subside, indicating a relaxation in the distal and proximal muscles 18 and 22 while the abdominal signal 66 remains at a high level.

At the end of the maneuver, when the subject relaxes, the abdominal signal 66 drops and there is again a reflexive increase in the EMG of the proximal and distal muscles 22 and 18, the distal signal 70 reaching a peak before the proximal signal 68.

The ability of the probe 10 of the present invention to distinguish between the activity of the proximal and distal muscles 22 and 18 with high resolution in time provides a detailed picture of the interaction of the muscles of the anal canal group. When the abdominal muscles tighten, there is an increase in intra-abdominal pressure which is accompanied by an immediate closing of the anal canal 14 as indicated by the increase of the EMG signals 68 and 70 and apparently an adaptive reflex which is part of the mechanism that prevents unwanted loss of either stool or urine when intra-abdominal pressure increases during "pushing" or other abdominal maneuvers such as coughing or lifting or straining. Moreover, because the distal muscles 18 contract more rapidly than do the proximal muscles 18, any material that might have moved from the rectum to the anal canal 14 is returned to the rectum through a kind of reverse peristalsis.

Interestingly, a similar sequence occurs at the end of the push. As the abdominal contracting diminishes, evidenced by signal 66, there is a rapid and prolonged contraction of the distal muscles 18 of the anal canal 14, which is followed by a contraction of the proximal muscles 22 of the anal canal 14. This distal-to-proximal sequence insures that material is returned to the rectum and the anal canal 14 is empty at the end of the maneuver. It is believed that if these cooperations between the various muscles do not occur in the proper sequence, or if they are absent, a number of problems can occur. For example, material can be trapped in the anal canal 14. The subsequent leakage of this material might produce inflammatory skin changes that could contribute to the development of the bowel disorder known as pruritus ani which is characterized by severe, and sometimes incapacitating, itching in the anal region. Similarly, in some individuals, the incoordination of these muscles may result in the disorder known as genuine stress incontinence, which is characterized by the pulsatile loss of urine on coughing, lifting, straining, etc.

The interactions of the various muscles of the anal canal group, shown in FIG. 5, are apparent only if the activities of the proximal and distal muscles 22 and 18 of the anal canal 14 can be isolated and examined over a very short time interval. Adequate time resolution can not be obtained by present digital radiographic techniques. Further, such radiographic techniques do not provide quantitative information on the magnitude of muscle contraction nor can they be used in conjunction with bio-feedback training. Present myographic electrodes do not recognize the distinctions between the activities of the distal and proximal muscles 18 and 22 and thus do not provide the isolated signals required to detect this cooperation.

The ability to isolate the myographic signals 70 and 68 from the distal and proximal muscles 18 and 22 of the anal canal 14 on a "real time" basis provides unexpected insight into the interaction of the anal canal muscle group not obtainable by present techniques.

The above description has been that of preferred embodiments of the present invention. It will occur to those who practice the art that any modifications may be made without departing from the spirit and scope of the invention. For example, additional electrode pairs may be placed on the insulating surface 12 to provide additional signal information along the anal canal 14 and the conductors of the pairs may be placed with different orientations than those described herein, provided independent signals may be obtained from each of the pairs. In order to apprise the public of the various embodiments that may fall within the scope of the invention, the following claims are made.

We claim:

1. An electrode assembly for substantially simultaneous myographic measurements of proximal and distal muscles at a first area adjacent to the distal muscles and a second area adjacent to the proximal muscles, the areas separated by a predetermined distance along the length of a canal extending through the proximal and distal muscles, said canal having an opening along the most distal side of the distal muscles, comprising:
   an elongate insulating support means having a first end for being received in a position at least the predetermined distance into the canal through the opening;
   a first electrode pair positioned on the outer surface of the insulating support for receiving myographic signals from the first area adjacent to the distal muscles when the insulating support is in the position within the canal and the first electrode pair is near the opening;
   a second electrode pair positioned on the outer surface of the insulating support and spaced by substantially the predetermined distance from the first electrode pair and positioned so that it is placed in contact with the proximal muscles of the canal for receiving myographic signals from the second area adjacent to the proximal muscles when the insulating support is in the position within the canal and the first electrode pair is near the opening;
   a tactile guide affixed to the elongate insulating support means and positioned so that it may remain outside of the canal when the elongate insulating support means is received in the canal for locating the first and second electrode pair at the distal and proximal muscles;
   wherein the elongate support is generally symmetric about an axis and wherein the electrode pairs are comprised of conductors opposed about the axis on the outside of the elongate support.

2. An electrode assembly according to claim 1 wherein the first and second electrode pairs are a conductive paint on the outer surface of the insulating support, and the first and second electrode pair communicate with an end of the insulating support outside of the canal by means of pathways of conductive paint, and
   wherein the pathways of conductive paint are on the outside of the insulating support and are covered with a nonconductive film.

3. A plurality of electrode assemblies for myographic measurements of proximal and distal muscles displaced by a distance along a canal extending through the proximal and distal muscles said canal having an opening along the most distal side of the distal muscles, each comprising:
   an elongate insulating support means having a first end for being received in a position at least the distance into the canal through the opening;
   a first electrode a pair positioned on the outer surface of the insulating support for receiving the myographic signals from the distal muscles when the insulating support is in the position within the canal and the first electrode pair is near the opening;
   a second electrode pair positioned on the outer surface of the insulating support the distance from the first electrode pair and positioned so that it is placed in contact with the proximal muscles of the canal for receiving myographic signals from the proximal muscles when the insulating support is in position within the canal and the first electrode pair is near the opening; and
   wherein the values of the distance are different for each electrode assembly and increase from a first given electrode assembly to a last given electrode assembly of the plurality of electrode assemblies.

4. The plurality of electrode assemblies recited in claim 3 wherein the values of the distance between the first and last given electrode are spaced by a constant increment.

5. The plurality of electrode assemblies recited in claim 4 wherein the constant increment is 0.5 cm.

6. An electrode assembly for substantially simultaneous myographic measurements of proximal and distal muscles at a first area adjacent to the distal muscles and a second area adjacent to the proximal muscles, the areas separated by a predetermined distance along the length of a canal extending through the proximal and distal muscles, said canal having an opening along the most distal side of the distal muscles comprising:
   an elongate insulating support means having a first end for being received in a position at least the predetermined distance into the canal through the opening;
   a first electrode pair positioned on the outer surface of the insulating support for receiving myographic signals from the first area adjacent to the distal muscles when the insulating support is in the position within the canal and the first electrode pair is near the opening;
   a second electrode pair positioned on the outer surface of the insulating support and spaced by substantially the predetermined distance from the first electrode pair and positioned so that it is placed in contact with the proximal muscles of the canal for receiving myographic signals from the second area adjacent to the proximal muscles when the insulating support is in the position within the canal and the first electrode pair is near the opening;

wherein the conductors of the first and second electrode pairs are a conductive paint on the outer surface of the insulating support, and the first and second electrode pair communicate with an end of the insulating support outside of the canal by means of a pathway of conductive paint; and wherein the pathways of conductive paint are on the outside of the insulating support and are covered with a nonconductive film.

7. A plurality of electrode assemblies for myographic measurements of proximal and distal muscles displaced by a distance along a canal extending through the proximal and distal muscles said canal having an opening along the most distal side of the distal muscles, each comprising:

an elongate insulating support means having a first end for being received in a position at least the distance into the canal through the opening;

a first electrode a pair positioned on the outer surface of the insulating support for receiving the myographic signals from the distal muscles when the insulating support is in the position within the canal and the first electrode pair is near the opening;

a second electrode pair positioned on the outer surface of the insulating support the distance from the first electrode pair and positioned so that it is placed in contact with the proximal muscles of the canal for receiving myographic signals from the proximal muscles when the insulating support is in position within the canal and the first electrode pair is near the opening;

wherein the values of the distance are different for each electrode assembly and increase from a first given electrode assembly to a last given electrode assembly of the plurality of electrode assemblies; and wherein the values of the distances between the first and last given electrode are spaced by a constant increment of 0.5 cm.

* * * * *